(12) United States Patent
Katsarava et al.

(10) Patent No.: US 8,765,164 B2
(45) Date of Patent: *Jul. 1, 2014

(54) POLY(ESTER UREA) POLYMERS AND METHODS OF USE

(75) Inventors: Ramaz Katsarava, Tbilisi (GE); David Tugushi, Tbilisi (GE); Zaza D. Gomurashvili, La Jolla, CA (US)

(73) Assignee: Kenneth W. Carpenter, San Diego, CA (US)

( * ) Notice: Subject to any disclaimer, the term of this patent is extended or adjusted under 35 U.S.C. 154(b) by 1902 days.

This patent is subject to a terminal disclaimer.

(21) Appl. No.: 11/584,143

(22) Filed: Oct. 19, 2006

(65) Prior Publication Data

US 2007/0128250 A1 Jun. 7, 2007

Related U.S. Application Data

(60) Provisional application No. 60/729,120, filed on Oct. 21, 2005.

(51) Int. Cl.
*A61K 31/56* (2006.01)
*C08F 20/00* (2006.01)
*A61F 2/02* (2006.01)

(52) U.S. Cl.
USPC ............................ 424/426; 514/182; 525/437

(58) Field of Classification Search
None
See application file for complete search history.

(56) References Cited

U.S. PATENT DOCUMENTS

| 4,443,563 A | 4/1984 | Dirlikov et al. ............... 521/174 |
| 6,210,441 B1 | 4/2001 | Flodin ....................... 623/13.18 |
| 6,221,997 B1 | 4/2001 | Woodhouse et al. ........... 528/61 |
| 6,342,300 B1 * | 1/2002 | Bengs et al. ............. 428/402.21 |
| 7,649,022 B2 * | 1/2010 | Gomurashvili et al. ...... 514/772 |
| 2004/0063606 A1 * | 4/2004 | Chu et al. ........................... 514/1 |
| 2006/0177416 A1 * | 8/2006 | Turnell et al. ............... 424/78.27 |
| 2006/0188486 A1 * | 8/2006 | Carpenter et al. ........... 424/93.7 |
| 2006/0286064 A1 * | 12/2006 | Turnell et al. ............... 424/78.27 |
| 2007/0077272 A1 * | 4/2007 | Li et al. ......................... 424/423 |
| 2007/0134332 A1 * | 6/2007 | Turnell et al. ................. 424/486 |
| 2007/0160622 A1 * | 7/2007 | Turnell et al. .............. 424/185.1 |

OTHER PUBLICATIONS

Kartvelishvili, Macromol. Chem. Phys., 198, 1997.*
Huang et al., "Biodegradable Polymers: Chymotrypsin Degradationi of a Low Molecular Weight Poly(ester-Urea) Containing Phenylalanine", *J. Appl. Polym. Sci*, 23, 429-437 (1979).
Yoneyama et al., "Synthesis and Properties of Poly(urea-ester)s Containing Amino Acid Residues in the Main Chain", *Polym. Prepr. Jpn.*, 43, 177 (1994).
Lipatova et al., "Biodestructing Segmented Polyurethanes Containing Amino Acid and Dipeptide Monomer Units in the Major Polymer Chain", *Dokl. Akad. Nauk SSSR*, 251(2):368 (1980).
Vysokomol, Soed., 31B(3):196 (1989) [no translation available].

* cited by examiner

*Primary Examiner* — Susan Tran
*Assistant Examiner* — William Craigo
(74) *Attorney, Agent, or Firm* — MediaVas LLC; Kenneth W. Carpenter (57) ABSTRACT

The invention provides high molecular weight, crystalline or semi crystalline biodegradable and biocompatible poly(ester urea) (PEU) polymers useful for making vascular stents and hard tissue replacement implants, such as bone substitutes. The PEU polymers are based on α amino acids and are made by a polycondensation reaction. PEU polymer compositions can contain a therapeutic diol incorporated into the polymer backbone that is released from such an implant in situ. Bioactive agents, such as analgesics, antibiotics, and the like, can also be covalently attached to certain PEU polymers for release into tissue surrounding an implant during biodegradation of the polymer.

22 Claims, 5 Drawing Sheets

POLY(ESTER UREA) POLYMERS AND METHODS OF USE

RELATED APPLICATION

This application relies for priority under 35 U.S.C. §119(e) on U.S. Ser. No. 60/729,120, filed Oct. 21, 2005, which is incorporated herein by reference.

FIELD OF THE INVENTION

The invention relates generally to polymer compositions and, in particular to bioabsorbable crystalline polymers useful as implantable polymer medical or surgical devices.

BACKGROUND INFORMATION

Bioabsorbable polymers with stability at ambient conditions, and high melting and softening temperatures are highly prized for various medical and pharmaceutical applications. Polymers that incorporate non-toxic, naturally occurring monomers into the polymer backbone are also preferred for such applications.

One class of α-amino acid-based polymers is poly(ester ureas) (PEUs), which are prepared from bis(α-aminoacyl)-α, ω-diol-diester monomers. Monomer contains two ester linkages per molecule, which can undergo either nonspecific (chemical) or specific (enzymatic) hydrolysis. The first attempt to use of this type of monomers (diamine monomers of α-amino acids in the form of bis(α-aminoacyl)-α,ω-diol-diester) for preparing bioabsorbable, semi-physiological PEUs was made in the late 1970s by S. J. Huang et al. (*J. Appl. Polym. Sci*, (1979) 23:429-437) and yielded a low molecular weight powdery polymer with Mn of 2000 Da and melting points in the range from 191-199° C. Hydrolytic degradation of these PEUs with various enzymes was also reported.

Later, Yoneyama et al. reported the synthesis of high molecular weight semi-physiological PEUs by the same route: Interaction of free bis(α-aminoacyl)-alkylene-diesters with non-physiological diisocyanates (*Polym. Prepr. Jpn.* (1994) 43:177). In some cases, high molecular weight PEUs were obtained with viscosities up to 0.7 dL/g.

Lipatova et al. have also synthesized semi-physiological poly(ester urethane ureas) from bis(L-phenylalanyl)-alkylene-diesters, diols and diisocyanates (Lipatova T. E. et al., *Dokl. Akad. Nauk SSSR* (1980) 251(2):368 and Gladyr II, et al. *Vysokomol. Soed*. (1989) 31B(3):196). However, no information on the synthesis of the starting material (for example., α-diamino diesters) was provided.

In 1997, Katsarava et al. (Kartvelishvili T, et al. *Macromol. Chem. Phys*. (1997) 198:1921-1932) published an account of synthesizing homo-PEUs (without using diisocyanates,) via active polycondensation, a process in which active carbonates (e.g. di-p-nitrophenyl carbonate) were interacted with di-p-toluenesulfonic acid salts of bis(α-amino acid)-α,ω-alkylene diesters. In this case, low-molecular-weight polymers were obtained. The low molecular weight of these polymers was attributed to intramolecular cyclization, resulting in hydantoin formation and, therefore, chain scission. Hydantoins are known as biocides. Biodegaradable PEUs containing hydantoin cycles may also possess innate antimicrobial activity.

Currently, however, modern research is aimed at investigating biodegradable polymer systems. These drug deliverers degrade into biologically acceptable compounds, often through the process of hydrolysis, and leave their incorporated medications behind. This erosion process occurs either in bulk (for example in case of poly(anhydrides), wherein the matrix degrades uniformly) or at the polymer's surface (whereby release rates are related to the polymer's surface area). The degradation process of well known aliphatic polyesters, PLLA or PLGA, involves the breakdown of these polymers into lactic and glycolic acids. These acids are eventually reduced by the Kreb's cycle to carbon dioxide and water, which the body can easily expel.

Regular AA-BB type amino acid based bio-analogous poly (ester amides) (PEAs) consisting of nontoxic building blocks, such as hydrophobic α-amino acids, aliphatic α,ω-diols, and aliphatic (fatty) dicarboxylic acids, have been investigated as biomaterials for drug release and tissue engineering applications (G. Tsitlanadze et al. *J. Biomater. Sci. Polymer Edn*, (2004) 15: 1-24). The combination in PEAs and PEURs of controlled enzymatic degradation and low rates of nonspecific hydrolysis makes these polymers attractive for drug delivery applications. In particular, PEAs appear to be blood and tissue compatible with advantageous properties for cardiovascular applications (K. DeFife et al. Transcatheter Cardiovascular Therapeutics—TCT 2004 Conference. Poster presentation. Washington D.C. (2004)).

In most drug-eluting applications, the drug is physically matrixed by dissolving or melting with a polymer. Another approach has also been reported in which a drug is chemically attached as a side group to a polymer.

If a drug or other therapeutic agent is covalently incorporated into a biodegradable polymer, a therapeutic polymer is formed. Such compositions represent synthetic polymers that combine therapeutic or palliative bioactivity with desirable mechanical and physical properties, and degrade into useful therapeutic active compounds. In other words, the compositions have the activity of a drug, but have the physical properties of a material. Recently, new therapeutic polyesters, polyamides, and poly(ester anhydrides) were reported, wherein non-steroidal anti inflammatory drugs (NSAIDs) were incorporated into a polymer backbone (R. C. Schmeltzer et al. *Biomacromolecules*. (2005) 6(1):359-367). In such compositions, drug release is directly dependent on the hydrolytic or enzymatic cleavage of polymer-drug binding groups. One of the advantages of a "backbone as a drug" polymer is that a high amount of drug or therapeutic compound can be incorporated into the structure.

Despite these advances in the art, there is a need for more and better polymer compositions and medical implants containing such compositions, wherein therapeutic molecules, such as drugs and other bioactive agents, are covalently attached to the polymer or incorporated into the backbones of polymer and release of the bioactive agents at a controlled rate is combined with desirable mechanical and physical properties of the polymer compositions.

SUMMARY OF THE INVENTION

The present invention is based on the discovery of a family of biodegradable poly(ester urea) polymers (PEUs) that can be used to formulate completely synthetic, and hence easy to produce, crystalline and semi-crystalline polymers of high molecular weight. These PEUs are useful as implantable surgical devices and for delivery to humans and other mammals of a variety of pharmaceutical and biologically active agents. The invention PEUs incorporate ester groups hydrolytically cleavable by bodily enzymes and non-toxic, naturally occurring monomers that contain amino acids in the polymer chains. In contrast to known poly(ester amides) (PEAs) and poly(ester urethanes) (PEURs), the invention PEUs are crystalline or semi-crystalline and possess advantageous mechanical, chemical and biodegradation properties. For example, the invention PEUs are characterized by high mechanical strength, and hydrolysis of the invention polymers can be catalyzed by enzymes present in physiological conditions, such as hydrolases.

Accordingly, in one embodiment the invention provides biodegradable polymers comprising at least one or a blend of PEUs having a chemical formula described by general structural formula (I):

Formula (I)

or general structural formula (II)

Formula (II)

wherein m is about 0.1 to about 0.9; p is about 0.9 to about 0.1; n is about 10 to about 150; $R^1$ is independently $(C_2-C_{20})$ alkylene, $(C_2-C_{20})$ alkenylene, $(C_2-C_8)$ alkyloxy, $(C_2-C_{20})$ alkylene, a residue of a saturated or unsaturated therapeutic diol, or a bicyclic-fragment of a 1,4:3,6-dianhydrohexitol of general formula (III):

Formula (III)

each $R^2$ is independently hydrogen, $(C_1-C_{12})$ alkyl or $(C_6-C_{10})$ aryl; the $R^3$s in an individual n or m monomer is independently hydrogen, $(C_1-C_6)$ alkyl, $(C_2-C_6)$ alkenyl, $(C_2-C_6)$ alkynyl, or $(C_6-C_{10})$ aryl $(C_1-C_6)$ alkyl; and $R^4$ is independently $(C_2-C_{20})$ alkyl or $(C_2-C_{20})$ alkenyl.

In another embodiment, the invention provides a biodegradable surgical device made using a polymer composition containing at least one or a blend of the invention crystalline or semi-crystalline PEUs described by general structural Formula (I) and Formula (II), wherein the device is implantable.

In still another embodiment, the invention provides a biocompatible, biodegradable PEU polymer formed by a polycondensation reaction of an α-amino acid, a p-toluenesulfonic acid monohydrate and a diol selected from $(C_2-C_{20})$ alkylene, $(C_2-C_{20})$ alkenylene, $(C_2-C_8)$ alkyloxy $(C_2-C_{20})$ alkylene diol, a saturated or unsaturated therapeutic diol; or a bicyclic-fragment of 1,4:3,6-dianhydrohexitol described by general formula (III), to obtain a PEU polymer described by general structural formula (I).

In yet another embodiment, the invention provides methods for synthesis of a biocompatible, biodegradable PEU by reacting in a polycondensation reaction an α amino acid, a p-toluenesulfonic acid monohydrate; and a diol selected from a $(C_2-C_{20})$ alkylene, $(C_2-C_{20})$ alkenylene, $(C_2-C_8)$ alkyloxy, $(C_2-C_{20})$ alkylene diol, a saturated or unsaturated therapeutic diol; or a bicyclic-fragment of 1,4:3,6-dianhydrohexitol described by general formula (III), to obtain a PEU having a chemical formula described by structural formula (I).

DETAILED DESCRIPTION OF THE INVENTION

The invention is based on the discovery of poly(ester urea) polymers (PEUs) of high mechanical strength that can be used to formulate completely synthetic, and hence easy to produce, crystalline and semi-crystalline polymers. These PEUs are useful in manufacture of implantable surgical devices and, in some embodiments, for delivery to humans and other mammals of a variety of therapeutic diols and bioactive agents. Due to structural properties, the invention PEUs biodegrade to release the incorporated therapeutic diols and bioactive agents at a controlled rate.

Accordingly, in one embodiment the invention provides biodegradable PEU polymers comprising at least one or a blend of PEUs having a chemical formula described by general structural formula (I):

Formula (I)

or general structural formula (II)

Formula (II)

wherein m is about 0.1 to about 0.9; p is about 0.9 to about 0.1; n is about 10 to about 150; $R^1$ is independently ($C_2$-$C_{20}$) alkylene, ($C_2$-$C_{20}$) alkenylene, ($C_2$-$C_8$) alkyloxy, ($C_2$-$C_{20}$) alkylene, a residue of a saturated or unsaturated therapeutic diol, or a bicyclic-fragment of a 1,4:3,6-dianhydrohexitol of general formula (III):

Formula (III)

each $R^2$ is independently hydrogen, ($C_1$-$C_{12}$) alkyl or ($C_6$-$C_{10}$) aryl; the $R^3$S in an individual n or m monomer are independently hydrogen, ($C_1$-$C_6$) alkyl, ($C_2$-$C_6$) alkenyl, ($C_2$-$C_6$) alkynyl, or ($C_6$-$C_{10}$) aryl ($C_1$-$C_6$) alkyl; and $R^4$ is independently ($C_2$-$C_{20}$) alkyl or ($C_2$-$C_{20}$) alkenyl.

In one embodiment, $R^4$ is independently ($C_3$ to $C_6$) alkyl or ($C_3$ to $C_6$) alkenyl, for example —$(CH_2)_4$—.

The bicyclic-fragments of 1,4:3,6-dianhydrohexitols can be derived from sugar alcohols, such as D-glucitol, D-mannitol, and L-iditol, such as 1,4:3,6-dianhydrosorbitol (DAS). In one alternative in the PEU polymer, at least one $R^1$ is a residue of a saturated or unsaturated therapeutic diol, or a bicyclic fragment of a 1,4:3,6-dianhydrohexitol, such as DAS. In yet another alternative in the PEU polymer, at least one $R^1$ is a bicyclic fragment of a 1,4:3,6-dianhydrohexitol, such as DAS.

As used herein, to describe the PEU polymers of structural formulas (I and II), the terms "amino acid" and "α-amino acid" mean a chemical compound containing an amino group, a carboxyl group and a R group, such as the $R^3$ groups defined herein. As used herein, the term "biological α-amino acid" means the amino acid(s) used in synthesis are selected from phenylalanine, leucine, glycine, alanine, valine, isoleucine, methionine, or a mixture thereof. Additional biological amino acids used in fabrication of co-polymers include lysine and ornithine, but are oriented in the polymer backbone adirectionally (i.e., in a non-biological orientation) such that the carboxyl group of the amino acid is pendent rather than being incorporated into a peptide bond. Additional adirectional amino acids can be incorporated into the invention compositions by varying the $R^4$ group as described herein.

In one alternative, at least one of the α-amino acids used in fabrication of the invention PEU polymers is a biological α-amino acid. For example, when the $R^3$s are $CH_2Ph$, the biological α-amino acid used in synthesis is L-phenylalanine. In alternatives wherein the $R^3$s are $CH_2$—$CH(CH_3)_2$, the polymer contains the biological α-amino acid, L-leucine. By varying the $R^3$s within monomers as described herein, other biological α-amino acids can also be used, e.g., glycine (when the $R^3$s are H), alanine (when the $R^3$s are $CH_3$), valine (when the $R^3$s are $CH(CH_3)_2$), isoleucine (when the $R^3$s are $CH(CH_3)$—$CH_2$—$CH_3$), phenylalanine (when the $R^3$s are $CH_2$—$C_6H_5$), or methionine (when the $R^3$s are —$(CH_2)_2$ $SCH_3$, and mixtures thereof. Additional biological amino acids used in fabrication of invention PEU polymers include lysine and ornithine, but are oriented in the polymer backbone adirectionally (i.e., in a non-biological orientation) such that the carboxyl group of the amino acid (which may be substituted by an $R^2$ other than H) is pendent rather than being incorporated into a peptide bond. Additional adirectional amino acids can be incorporated into the invention compositions by varying the $R^4$ group as described herein.

In yet another alternative embodiment, all of the various α-amino acids contained in the polymers used in making the invention PEU polymers are biological α-amino acids, as described herein.

In still a further embodiment, at least one of the $R^3$s further can be —$(CH_2)_3$— wherein the $R^3$s cyclize to form the chemical structure described by structural formula (XIV):

Formula (XIV)

When the $R^3$s are —$(CH_2)_3$—, an α-amino acid analogous to pyrrolidine-2-carboxylic acid (proline) is used.

The term "aryl" is used with reference to structural formulas herein to denote a phenyl radical or an ortho-fused bicyclic carbocyclic radical having about nine to ten ring atoms in which at least one ring is aromatic. In certain embodiments, one or more of the ring atoms can be substituted with one or more of nitro, cyano, halo, trifluoromethyl, or trifluoromethoxy. Examples of aryl include, but are not limited to, phenyl, naphthyl, and nitrophenyl.

The term "alkenylene" is used with reference to structural formulas herein to mean a divalent branched or unbranched hydrocarbon chain containing at least one unsaturated bond in the main chain or in a side chain.

As used herein the term "bioactive agent" means a bioactive agent as disclosed herein that is not incorporated into the polymer backbone. One or more such bioactive agents may be included in the invention PEU polymer compositions. As used herein, the term "dispersed" as used to refer to bioactive agents means that the bioactive agent is dispersed, mixed, dissolved, homogenized, and/or covalently bound ("dispersed") in a polymer, for example attached to a functional group in the PEU polymer of the composition or to the surface of a polymer particle, but not incorporated into the backbone of a PEU polymer. To distinguish backbone-incorporated therapeutic diols from those that are not incorporated into the polymer backbone, (as a residue thereof), such dispersed therapeutic or palliative agents are referred to herein as "bioactive agent(s)" and may be contained within polymer conjugates or otherwise dispersed in the PEU polymer composition, as described below. Such bioactive agents may include, without limitation, small molecule drugs, peptides, proteins, DNA, cDNA, RNA, sugars, lipids and whole cells. The bioactive agents are administered in polymer compositions, such as polymer depots, particles or surgical devices having a variety of sizes and structures suitable to meet differing therapeutic goals and routes of administration.

As used herein, a "therapeutic diol" means any diol molecule, whether synthetically produced, or naturally occurring (e.g., endogenously) that affects a biological process in a mammalian individual, such as a human, in a therapeutic or palliative manner when administered to the mammal. The residues of such therapeutic diols are contained in the backbone of the invention PEU polymers.

As used herein, the term "residue of a therapeutic diol" means a portion of a therapeutic diol, as described herein, which portion excludes the two hydroxyl groups of the diol. The corresponding therapeutic diol containing the "residue" thereof is used in synthesis of the PEU polymers described herein. The residue of the therapeutic diol is reconstituted in vivo (or under similar conditions of pH, aqueous media, and the like) to the corresponding diol upon release in a controlled manner from the backbone of the polymer by biodegradation. The rate of biodegradation of the invention PEUs and surgical devices containing such polymers depends upon such factors as the properties of the building blocks of the polymer used in synthesis of the PEU polymer and the properties of the enzyme-containing solution to which the polymer is subjected during biodegradation, which properties are as known in the art and as described herein.

As used herein the term "bioactive agent" means a bioactive agent as disclosed herein that is not incorporated into the polymer backbone, and a therapeutic diol that is not incorporated into the polymer backbone is also referred to herein as a bioactive agent. One or more such bioactive agents may optionally be included in the invention PEU polymer compositions.

As used herein to refer to bioactive agents, the term "dispersed" means that the bioactive agent is dissolved into, homogenized or intermixed with, and/or covalently bound to an invention PEU polymer in a PEU polymer composition, for example attached to a functional group in the polymer of the composition or to the surface of a polymer particle or surgical device, but not incorporated into the backbone of a PEU polymer.

The term, "biodegradable" as used to describe the invention PEU polymers and compositions (e.g., particles or surgical devices containing such polymers) means the polymer is broken down into innocuous and therapeutic products in the normal functioning of the mammalian body. The invention PEUs are crystalline polymers having enzymatically hydrolyzable aliphatic ester linkages, which provide biodegradability, and are typically chain terminated predominantly with amino groups. Thus, in the case of a PEU that contains the residue of a naturally occurring therapeutic diol in the backbone, the breakdown products include the naturally occurring therapeutic diol. The break down products of a PEU polymer composition may also include as any bioactive agents dispersed in the polymer.

PEU polymers and various compositions (e.g., particles or devices) made using the invention PEU polymers biodegrade by enzymatic action at the surface. In an enzymatic solution, such as a protease or under physiologic conditions, a uniform erosive behavior has been observed. (FIG. 6). In addition, the invention PEU polymers display no hydrolytic degradation when tested in a saline (PBS) medium. Therefore, release of a backbone incorporated therapeutic diol or a dispersed bioactive agent to the subject is at a smooth rate that approximates zero order kinetics over a prolonged period. Invention PEU polymers also have a longer shelf life than, for example, poly(glycolic acid) or poly(lactic acid), or their copolymers.

The PEU polymers used in the invention implantable particles and surgical devices can be designed to tailor the rate of biodegradation of the polymer to result in continuous contact of the surrounding tissue with an incorporated therapeutic diol or bioactive agent over a selected period of time. For instance, the polymer in the device will degrade over a time selected from about two weeks to about six years, more specifically nine weeks to two years, or six months to one year or longer, depending on such factors as the size of the implant, the type of ester linkage formed by various amino acid residues and the degree of crystallinity of a given polymer, with a crystalline polymer degrading more slowly than a semi-crystalline or amorphous polymer. The subject's endogenous processes biodegrade the polymer backbone so as to release an incorporated therapeutic diol, as well as any bioactive agents conjugated to the polymer. The fragile therapeutic diols and optional bioactive agents are protected by the more slowly biodegrading polymer to increase half-life and persistence thereof locally at the site of the polymer implantation. In one embodiment, the PEU polymer is crystalline and a surgical device made thereof is completely biodegradable.

The term "biocompatible" as used to describe the invention PEU polymers, as well as compositions, particles, and devices made using such polymers, means no harmful breakdown products are made during biodegradation thereof. The PEU polymers described herein break down in vivo via enzymes common in physiological conditions, such as proteases, to ultimately produce amino acids, readily metabolized diols, and $CO_2$, biocompatible compounds. Therefore, the invention semi-crystalline polymer compositions are substantially non-inflammatory, either locally or systemically. In addition, the polymers disclosed herein that incorporate the residue of a therapeutic diol, upon enzymatic degradation, provide the reconstituted therapeutic diol, and essential amino acids that may nurture cells. Uptake of the polymer is generally safe: studies have shown that mammals can metabolize/clear the polymer degradation products. These polymers and the medical implants fabricated therefrom are, therefore, substantially non-inflammatory to the subject both at the site of implant and systemically. Biocompatibility is optimized when the α-amino acids in the invention PEU polymers are all biological α-amino acids.

In addition to the therapeutic diol released from the polymer backbone during degradation of the polymers, the polymer molecules may optionally have bioactive agent(s) conjugated thereto via a linker or covalently attached to the polymer (i.e., not incorporated into the polymer backbone). Optionally, the amino termini of the invention PEUs can be acetylated or otherwise capped by conjugation to any other acid-containing, biocompatible molecule, to include without restriction organic acids, bioinactive biologics, other polymers, and bioactive agents as described herein.

For example, a polymer bearing free carboxyl groups can readily react with an amino moiety, thereby covalently bonding a peptide to the polymer via the resulting amide group. As will be described herein, the biodegradable polymer and a desired bioactive agent may contain numerous complementary functional groups that can be used to covalently attach the bioactive agent to the biodegradable polymer.

In addition to treatment of humans, the invention implantable polymer compositions and surgical devices fabricated therefrom are also intended for use in veterinary treatment of a variety of mammalian patients, such as pets (for example, cats, dogs, rabbits, and ferrets), farm animals (for example, swine, horses, mules, dairy and meat cattle) and race horses.

Methods for making polymers containing α-amino acids in the general formula are well known in the art. For example, for the embodiment of the polymer of formula (I) or (II), the α-amino acid can be converted into a bis(α-amino acid)-α, ω-diol-diester monomer, for example, by condensing the α-amino acid with a diol HO—R$^1$—OH. As a result, ester bonds are formed. For synthesis of PEU polymers, an acid chloride of carbonic acid (phosgene, diphosgene, triphosgene) is entered into a polycondensation reaction with a di-p-toluenesulfonic acid salt of a bis(α-amino acid)-alkylene diester to obtain the final polymer having both ester and urea bonds. In the present invention, at least one therapeutic diol can be used in the polycondensation protocol.

The unsaturated PEUs can be prepared by interfacial solution condensation of di-p-toluenesulfonate salts of bis(α-amino acid)-alkylene diesters, comprising at least one double bond in R$^1$. Unsaturated diols useful for this purpose include, for example, 2-butene-1,4-diol and 1,18-octadec-9-en-diol. Unsaturated monomer can be dissolved prior to the reaction in alkaline water solution, e.g. sodium hydroxide solution. The water solution can then be agitated intensely, under external cooling, with an organic solvent layer, for example chloroform, which contains an equimolar amount of monomeric, dimeric or trimeric phosgene. An exothermic reaction proceeds rapidly, and yields a polymer that (in most cases) remains dissolved in the organic solvent. The organic layer can be washed several times with water, dried with anhydrous sodium sulfate, filtered, and evaporated. Unsaturated PEUs with a yield of about 75%-85% can be dried in vacuum, for example at about 45° C.

Salts of p-toluene sulfonic acid are known for use in synthesizing polymers containing amino acid residues. The aryl sulfonic acid salts are used instead of the free base because the aryl sulfonic salts of bis(α-amino acid)-alkylene-diesters are easily purified through recrystallization and render the amino groups as unreactive ammonium tosylates throughout workup. In the interfacial polycondensation reaction, the nucleophilic amino group is readily revealed through the addition of an inorganic base, such as NaOH, NaHCO$_3$, Na$_2$CO$_3$, and the like, or, rarely, in an organic base, such as triethylamine, so the polymer product is obtained in high yield. Slight excess of triethylamine can act as catalyst as well.

For example, (0.05 mol) of di-aryl sulfonic acid salts of bis(α-amino acid) diesters can be dissolved prior the reaction in a solution of 13.25 g (0.125 mol) of sodium carbonate solution in 70 mL water and with vigorous stirring added to a solution of 4.95 g (0.05 mol) phosgene in 200 mL dry chloroform. The poly(ester urea) forms rapidly and heat is evolved. After the reaction has been stirred briskly for 10 min, the chloroform layer can be evaporated. Residual polymer can be washed several times with water and vacuum-dried.

The di-aryl sulfonic acid salts of bis(α-amino acid) diesters can be prepared by admixing α-amino acid, p-aryl sulfonic acid (e.g. p-toluene sulfonic acid monohydrate), and saturated or unsaturated diol in benzene or toluene, heating to reflux temperature, until water evolution is finished, then cooling. The unsaturated diols useful for this purpose include, for example, 2-butene-1,3-diol and 1,18-octadec-9-en-diol.

Synthesis of the unsaturated poly(ester-urea)s (UPEUs) useful as high molecular weight biodegradable polymers of the structural formula (II) as disclosed above will now be described. A presently preferred reactant is p-toluene sulfonic acid salt of Lysine benzyl ester. The benzyl ester protecting group is preferably removed to confer functionality, but it should not be removed by hydrogenolysis because hydrogenolysis would saturate the desired double bonds; rather the benzyl ester group should be converted to an acid group by a method that would preserve unsaturation. To remove a benzyl group in the presence of double bonds, trifluoroacetic acid (CF$_3$COOH) can be used. Alternatively, the lysine reactant can be protected by a protecting group different from benzyl that can be readily removed in the finished product while preserving unsaturation, e.g., a lysine reactant can be protected with t-butyl (i.e., the reactant can be t-butyl ester of lysine) and the t-butyl can be converted to H while preserving unsaturation by treatment of the product with acid. However, the synthesis of t-butyl esters as p-toluenesulfonic acid salts is rather problematic.

In unsaturated compounds having structural formula (II), the following hold: An amino substituted aminoxyl (N-oxide) radical bearing group e.g., 4-amino TEMPO, can be attached using carbonyldiimidazole, or suitable carbodiimide, as a condensing agent. Bioactive agents, and the like, as described herein, optionally can be attached via the double bond functionality provided that the therapeutic diol residue in the polymer composition does not contain a double or triple bond.

For example, the invention high molecular weight semi-crystalline PEUs having structural formula (I) can be prepared inter-facially by using phosgene as a bis-electrophilic monomer in a chloroform/water system, as shown in the reaction scheme below:

For example, for synthesis of the polymer of structural formula (I), the α-amino acid with pendant R$^3$ can be converted through esterification into a bis-α,ω-diamine, for example, by condensing the α-amino acid containing pendant R$^3$ with a diol HO—R$^1$—OH. As a result, di-ester monomers with reactive α,ω-amino groups are formed. Then, the bis-α,ω-diamine is entered into a polycondensation reaction with chlorides of carbonic acid, to obtain a final polymer having both ester and urea bonds (a PEU).

copoly(ester ureas) containing L-Lysine esters and having structural formula (II) can be carried out by similar scheme:

(II)

20% solution of phosgene (ClCOCl) (highly toxic) in toluene, for example (commercially available (Fluka Chemie, GMBH, Buchs, Switzerland), can be substituted either by diphosgene (trichloromethylchloroformate) or triphosgene (bis(trichloromethyl)carbonate). Less toxic carbonyldiimidazole can be also used as a bis-electrophilic monomer instead of phosgene, di-phosgene, or tri-phosgene.

General Procedure for Synthesis of PEUs

It is necessary to use cooled solutions of monomers to obtain PEUs of high molecular weight. For example, to a suspension of di-p-toluenesulfonic acid salt of bis(α-amino acid)-α,ω-alkylene diester in 150 mL of water, anhydrous sodium carbonate is added, stirred at room temperature for about 30 minutes and cooled to about 2-0° C., forming a first solution. In parallel, a second solution of phosgene in chloroform is cooled to about 15-10° C. The first solution is placed into a reactor for interfacial polycondensation and the second solution is quickly added at once and stirred briskly for about 15 min. Then chloroform layer can be separated, dried over anhydrous Na$_2$SO$_4$, and filtered. The obtained solution can be stored for further use.

All the exemplary PEU polymers fabricated were obtained as solutions in chloroform and these solutions are stable during storage. However, some polymers, for example, 1-Phe-4, become insoluble in chloroform after separation. To overcome this problem, polymers can be separated from chloroform solution by casting onto a smooth hydrophobic surface and allowing chloroform to evaporate to dryness. No further purification of obtained PEUs is needed. The yield and characteristics of exemplary PEUs obtained by this procedure are summarized in Table 1 below.

General Procedure for Preparation of Porous PEUs.

To obtain a porous, bone-like material useful as a bone substitute L-Leu based PEUs, such as 1-L-Leu-4 and 1-L-Leu-6, can be fabricated using the general procedure described below. Such procedure is less successful in formation of a porous bone-like material when applied to L-Phe based PEUs.

The reaction solution or emulsion (about 100 mL) of PEU in chloroform, as obtained just after interfacial polycondensation, is added dropwise with stirring to 1,000 mL of about 80° C.-85° C. water in a glass beaker, preferably a beaker made hydrophobic with dimethyldichlorsilane to reduce the adhesion of PEU to the beaker's walls. The polymer solution is broken in water into small drops and chloroform evaporates rather vigorously. Gradually, as chloroform is evaporated, small drops combine into a compact tar-like mass that is transformed into a sticky rubbery product. This rubbery product is removed from the beaker and put into hydrophobized cylindrical glass-test-tube, which is thermostatically controlled at about 80° C. for about 24 hours. Then the test-tube is removed from the thermostat, cooled to room temperature, and broken to obtain the polymer. The obtained porous bar is placed into a vacuum drier and dried under reduced pressure at about 80° C. for about 24 hours. In addition, any procedure known in the art for obtaining porous polymeric materials can also be used.

Properties of high-molecular-weight porous PEUs made by the above procedure yielded results as summarized in Table 1.

TABLE 1

Properties of PEU Polymers of Formula (I).

| PEU* | Yield [%] | $\eta_{red}{}^{a)}$ [dL/g] | $M_w{}^{b)}$ | $M_n{}^{b)}$ | $M_w/M_n{}^{b)}$ | $Tg^{c)}$ [° C.] | $T_m{}^{c)}$ [° C.] |
|---|---|---|---|---|---|---|---|
| 1-L-Leu-4 | 80 | 0.49 | 84000 | 45000 | 1.90 | 67 | 103 |
| 1-L-Leu-6 | 82 | 0.59 | 96700 | 50000 | 1.90 | 64 | 126 |
| 1-L-Phe-6 | 77 | 0.43 | 60400 | 34500 | 1.75 | — | 167 |
| [1-L-Leu-6]$_{0.75}$-[1-L-Lys(OBn)]$_{0.25}$ | 84 | 0.31 | 64400 | 43000 | 1.47 | 34 | 114 |
| 1-L-Leu-DAS | 57 | 0.28 | 55700$^{d)}$ | 27700$^{d)}$ | 2.1$^{d)}$ | 56 | 165 |

*In general PEU formula (I)  1-L-Leu-4 = R$^1$ = (CH$_2$)$_4$, R$^3$ = i-C$_4$H$_9$
  1-L-Leu-6 = R$^1$ = (CH$_2$)$_6$, R$^3$ = i-C$_4$H$_9$
  1-L-Phe-6: = .R$^1$ = (CH$_2$)$_6$, R$^3$ = —CH$_2$—C$_6$H$_5$.
In general formula (III)  1-L-Leu-DAS = R$^1$ = 1,4:3,6-dianhydrosorbitol, R$^3$ = i-C$_4$H
$^{a)}$Reduced viscosities were measured in DMF at 25° C. and a concentration 0.5 g/dL
$^{b)}$GPC Measurements were carried out in DMF, (PMMA)
$^{c)}$Tg taken from second heating curve from DSC Measurements (heating rate 10° C./min).
$^{d)}$GPC Measurements were carried out in DMAc, (PS)

Accordingly, in yet another embodiment, the invention provides a biocompatible, biodegradable polymer of Formula (I) formed by a polycondensation reaction of an α amino acid, a p-toluenesulfonic acid monohydrate; and a diol selected from a (C$_2$-C$_{20}$) alkylene, (C$_2$-C$_{20}$) alkenylene, (C$_2$-C$_8$) alkyloxy (C$_2$-C$_{20}$) alkylene diol, a saturated or unsaturated therapeutic diol; or a bicyclic-fragment of 1,4:3,6-dianhydrohexitol of general formula (III), Formula (III)

For example, the α-amino acid can be L-lysine and the diol can be a saturated or unsaturated therapeutic diol. In one embodiment, the diol is a bicyclic-fragment of 1,4:3,6-dianhydrohexitol, such as D-glucitol, D-mannitol, and L-iditol. For formation of an invention polymer composition of structural formula (II), the polycondensation reaction further includes a di-p-toluenesulfonic acid salt of an α-amino acid benzyl ester, such as L-lysine benzyl ester.

The biodegradable PEU polymers and copolymers of structural formula (I) may contain one amino acid per monomer, are crystalline or semi-crystalline, have weight average molecular weights ranging from about 2000 to about 300,000 and typically have reduced viscosities at 25° C., determined by an automated Ubbelohde capillary viscometer, ranging from about 0.15 dL/g to about 3.5 dL/g, for example, ranging from 0.4 dL/g to 2.5 dL/g.

The biodegradable PEU polymers of structural formula (II) may contain up to two amino acids per monomer, are semi-crystalline or crystalline, have weight average molecular weights ranging from about 2000 to about 300,000 and typically have reduced viscosities at 25° C., determined by an automated Ubbelohde capillary viscometer, ranging from about 0.15 to about 3.5 dL/g, for example, ranging from 0.4 to 2.5 dL/g.

In still another embodiment the invention provides methods for synthesis of a biocompatible, biodegradable polymer of formula (I) comprising a polycondensation reaction of:

an α-amino acid, a p-toluenesulfonic acid monohydrate; and a diol selected from a $(C_2-C_{20})$-alkylene, $(C_2-C_{20})$ alkenylene, $(C_2-C_8)$ alkyloxy $(C_2-C_{20})$ alkylene diol, a saturated or unsaturated therapeutic diol; or a bicyclic-fragment of 1,4:3,6-dianhydrohexitol of general formula (III), Formula (III)

The preferred α-amino acid for this purpose is L-lysine, although any other amino acid as disclosed herein can be used. To provide therapeutic properties to the polymer, the diol can be selected from saturated or unsaturated therapeutic diols, such as is described herein. Alternatively, the diol can be selected from bicyclic-fragment of 1,4:3,6-dianhydrohexitols, such as D-glucitol, D-mannitol, or L-iditol. For production of a polymer of Formula (II), the reaction product so produced is further subjected to a polycondensation reaction with a di-p-toluenesulfonic acid salt of an α amino acid benzyl ester. In one embodiment, the α amino acid benzyl ester is L-lysine benzyl ester, although any other amino acid as disclosed herein can be used.

The invention PEU polymers can be fabricated in a variety of molecular weights, and the appropriate molecular weight for a desired use is readily determined by one of skill in the art by judicious selection of the polymer building blocks and by selection of the number of n units contained in the polymer. Thus, e.g., a suitable molecular weight will be on the order of about 5,000 to about 300,000, for example about 5,000 to about 250,000, or about 75,000 to about 200,000, or about 100,000 to about 150,000.

The molecular weights and polydispersities herein are determined by gel permeation chromatography (GPC) using polystyrene standards. More particularly, number and weight average molecular weights ($M_n$ and $M_w$) are determined, for example, using a Model 510 gel permeation chromatography (Water Associates, Inc., Milford, Mass.) equipped with a high-pressure liquid chromatographic pump, a Waters 486 UV detector and a Waters 2410 differential refractive index detector. Solution of 0.1% LiCl in N,N-dimetylformamide (DMF) or N,N-dimethylacetamide (DMAc) is used as the eluent (1.0 mL/min). Polystyrene (PS) or poly(methyl methacrylate) (PMMA) standards having a narrow molecular weight distribution were used for calibrations.

Polymer glass transition (Tg) and melting temperatures (Tm) can be determined using any means known in the art, for example by differential scanning calorimetry (DSC) using a Mettler Toledo DSC 822e (Mettler Toledo Inc. Columbus, Ohio) differential scanning calorimeter. For measurement, the samples disclosed herein were placed in aluminum pans. Measurements were carried out at a scanning rate of 10° C./min under nitrogen flow. Elemental Analysis of PEUs was conducted in Numega Labs, San Diego, Calif.

Polymers of general structural formula (II) bear functionalities that allow facile covalent attachment of bioactive agents to the polymer. For example, a polymer bearing carboxyl groups can readily react with an amino moiety, thereby covalently bonding the peptide to the polymer via the resulting amide group. As will be described herein, the biodegradable polymer and the peptide may contain numerous complementary functional groups that can be used to covalently attach the peptide to the biodegradable polymer. However, invention polymers of general structural formula (I) are not suitable for covalent attachment of bioactive agents to the polymer.

The invention PEUs of structural formula (II) have built-in functional groups on PEU backbones, and these built-in functional groups can react with other chemicals and lead to the incorporation of additional functional groups to expand the functionality of such polymers further. Therefore, such polymers used in the invention methods are ready for reaction with bioactive agents, without the necessity of prior modification.

Therefore, at least one bioactive agent optionally can be covalently bound to the biodegradable polymers of structural formula (II) via a wide variety of suitable functional groups. For example, when the biodegradable polymer contains an amino acid, the carboxyl group of the amino acid can be used to react with a complimentary moiety on the bioactive agent, such as hydroxy, amino, thio, and the like. A wide variety of suitable reagents and reaction conditions are disclosed, e.g., in *March's Advanced Organic Chemistry, Reactions, Mechanisms, and Structure*, Fifth Edition, (2001); and *Comprehensive Organic Transformations*, Second Edition, Larock (1999).

In other embodiments, a bioactive agent can be linked to any of the polymers of structure (II) through an amide, ester, ether, amino, ketone, thioether, sulfinyl, sulfonyl, disulfide linkage. Such a linkage can be formed from suitably functionalized starting materials using synthetic procedures that are known in the art.

For example, in one embodiment a bioactive agent can be linked to the polymer via a carboxyl group (e.g., COOH) of the polymer. Specifically, a compound of structure (II) wherein $R_2$=H can react with an amino functional group or a hydroxyl functional group of a peptide to provide a biodegradable polymer having the peptide attached via an amide linkage or carboxylic ester linkage, respectively. In another embodiment, the carboxyl group of the polymer can be transformed into an acyl halide, acyl anhydride, "mixed" anhydride, or active ester. In other embodiments, the free —$NH_2$ terminal regions of the polymer molecule can be acylated to assure that the peptide will attach only via a lateral carboxyl group of the polymer and not to the free ends of the polymer. For example, the invention crystalline composition described herein can be prepared from PEU (Formula I) where the N-terminal free amino groups are acylated with anhydride RCOOCOR, where the R=$(C_1-C_{24})$ alkyl.

Alternatively, the bioactive agent may be attached to the PEU polymer via a linker molecule, as described herein. Indeed, to improve surface hydrophobicity of the biodegradable polymer, to improve accessibility of the biodegradable polymer towards enzyme activation, and to improve the release profile of the biodegradable polymer, a linker may be utilized to indirectly attach the bioactive agent to the biodegradable polymer. In certain embodiments, the linker compounds include poly(ethylene glycol) having a molecular weight ($M_w$) of about 44 to about 10,000, preferably 44 to 2000; amino acids, such as serine and β, γ, or δ, amino acids; polypeptides with repeat units from 1 to 100; and any other suitable low molecular weight polymers. The linker typically separates the bioactive agent from the polymer by about 5 angstroms up to about 200 angstroms.

In still further embodiments, the linker is a divalent radical of formula W-A-Q, wherein A is ($C_1$-$C_{24}$)alkyl, ($C_2$-$C_{24}$) alkenyl, ($C_2$-$C_{24}$)alkynyl, ($C_3$-$C_8$)cycloalkyl, or ($C_6$-$C_{10}$) aryl, and W and Q are each independently —N(R)C(=O)—, —C(=O)N(R)—, —OC(=O)—, —C(=O)O, —O—, —S—, —S(O), —S(O)$_2$—, —S—S—, —N(R)—, —C(=O)—, wherein each R is independently H or ($C_1$-$C_6$) alkyl.

As used to describe the above linkers, the term "alkyl" refers to a straight or branched chain hydrocarbon group including methyl, ethyl, n-propyl, isopropyl, n-butyl, isobutyl, tert-butyl, n-hexyl, and the like.

As used herein to describe the above linkers, "alkenyl" refers to straight or branched chain hydrocarbon groups having one or more carbon-carbon double bonds.

As used herein to describe the above linkers, "alkynyl" refers to straight or branched chain hydrocarbon groups having at least one carbon-carbon triple bond.

As used herein to describe the above linkers, "aryl" refers to aromatic groups having in the range of 6 up to 14 carbon atoms.

In certain embodiments, the linker may be a polypeptide having from about 2 up to about 25 amino acids. Suitable peptides contemplated for use include homo-poly(amino acids): poly-L-lysine, poly-L-glutamic acid, poly-L-aspartic acid, poly-L-histidine, poly-L-ornithine, poly-L-threonine, poly-L-tyrosine, poly-L-leucine, poly-L-lysine-L-phenylalanine, poly-L-arginine, poly-L-lysine-L-tyrosine, and the like.

The linker can be attached first to the polymer or to the bioactive agent. During synthesis, the linker can be either in unprotected form or protected form, using a variety of protecting groups well known to those skilled in the art. In the case of a protected linker, the unprotected end of the linker can first be attached to the polymer or the bioactive agent. The protecting group can then be de-protected using Pd/$H_2$ hydrogenolysis, mild acid or base hydrolysis, or any other common de-protection method that is known in the art. The de-protected linker can then be attached to the bioactive agent.

Polymer/Bioactive Agent Linkage

In one embodiment, the biodegradable, high molecular weight polymer compositions as described herein and as used in making implantable surgical devices can have at least one bioactive agent directly linked to the polymer. The residues of the polymer can be linked to the residues of one or more bioactive agents. For example, one residue of the polymer can be directly linked to one residue of the bioactive agent, the polymer and the bioactive agent each having one open valence. Alternatively, more than one bioactive agent, or a mixture of bioactive agents can be directly linked to the polymer. However, since the residue of each bioactive agent can be linked to a corresponding residue of the polymer, the number of residues of the one or more bioactive agents can be no more than the number of open valences on the residue of the polymer.

As used herein, a "residue of a polymer" refers to a radical of a polymer of structure (I or II) having one or more open valences. Any synthetically feasible atom, atoms, or functional group of the polymer (e.g., on the polymer backbone or pendant group) of the present invention can be removed to provide the open valence, provided bioactivity is substantially retained when the radical is attached to a residue of a bioactive agent. Additionally, any synthetically feasible functional group (e.g., carboxyl) can be created on the polymer (e.g., on the polymer backbone or pendant group) to provide the open valence, provided bioactivity is substantially retained when the radical is attached to a residue of a bioactive agent. Based on the linkage that is desired, those skilled in the art can select suitably functionalized starting materials that can be derived from the polymer of the present invention using procedures that are known in the art.

For example, the residue of a bioactive agent can be linked to the residue of a compound of structural formula (II) and (III) through an amide (e.g., —N(R)C(=O)— or —C(=O) N(R)—), ester (e.g., —OC(=O)— or —C(=O)O—), ether (e.g., —O—), amino (e.g., —N(R)—), ketone (e.g., —C(=O)—), thioether (e.g., —S—), sulfinyl (e.g., —S(O)—), sulfonyl (e.g., —S(O)$_2$—), disulfide (e.g., —S—S—), or a direct (e.g., C—C bond) linkage, wherein each R is independently H or ($C_1$-$C_6$)alkyl. Such a linkage can be formed from suitably functionalized starting materials using synthetic procedures that are known in the art. Based on the linkage that is desired, those skilled in the art can select suitably functional starting material that can be derived from a residue of a compound of structural formulae (II) and from a given residue of a bioactive agent using procedures that are known in the art. The residue of the bioactive agent can be linked to any synthetically feasible position on the residue of a compound of structural formula (II). Additionally, the invention also provides compounds having more than one residue of a bioactive agent directly linked to a compound of structural formula (II).

The number of bioactive agents that can be linked to the polymer molecule typically depends upon the molecular weight of the polymer. For example, for a compound of structural formula (I), wherein n is about 5 to about 150, preferably about 5 to about 70, up to about 150 bioactive agents (i.e., residues thereof) can be directly linked to the polymer (i.e., residue thereof) by reacting the bioactive agent(s) with end groups of the polymer. In unsaturated polymers, the peptidic antigens can also be reacted with double (or triple) bonds in the polymer.

Factors that typically affect the release rate of the bioactive agent from the polymer are the nature and amount of the polymer, the types of polymer/bioactive agent linkage, and the nature and amount of additional substances present in the formulation.

The compositions used in the invention methods optionally comprise an "effective amount" of a residue of a therapeutic diol or of a bioactive agent of interest. That is, an amount will be included in the compositions that will cause the subject to produce a sufficient immunological response in order to prevent, reduce or eliminate symptoms. The exact amount will vary, depending on the subject being treated; the age and general condition of the subject to be treated; the capacity of the subject's immune system to synthesize antibodies; the degree of therapeutic or palliative treatment desired; the severity of the condition being treated; and the particular therapeutic diol or bioactive agent included in the composition and its mode of operation, among other factors. An appropriate effective amount can be readily determined by one of skill in the art. Thus, an "effective amount" will fall in a relatively broad range that can be determined through routine trials. For example, for purposes of the present invention, an effective dose will typically range from about 1 µg to about 100 mg, for example from about 5 µg to about 1 mg, or about 10 µg to about 500 µg of the therapeutic diol or bioactive agent delivered per dose.

Therapeutic Diols

Suitable therapeutic diols that can be used to prepare bis (alpha-amino acid) diesters of therapeutic diol monomers for introduction into the invention polymer compositions include naturally occurring therapeutic diols, such as 17-β-estradiol, a natural and endogenous hormone, useful in preventing restenosis and tumor growth (Yang, N. N., et al. Identification of an estrogen response element activated by metabolites of 17-β-estradiol and raloxifene. *Science* (1996) 273, 1222-1225; Parangi, S., et al., Inhibition of angiogenesis and breast cancer in mice by the microtubule inhibitors 2-methoxyestradiol and taxol, *Cancer Res*. (1997) 57, 81-86; and Fotsis, T., et al., The endogenous oestrogen metabolite 2-methoxyoestradiol inhibits angiogenesis and suppresses tumor growth, *Nature* (1994) 368, 237-239). The safety profiles of such endogenously occurring therapeutic diol molecules are believed to be superior to those of synthetic and/or non-endogenous molecules having a similar utility, such as sirolimus.

For example, a therapeutic diol, such as active steroid hormone 17-β-estradiol containing mixed hydroxyls—secondary and phenolic—can be incorporated into the backbone of a PEU polymer used to make a surgical implant, such as a stent body. When the PEU polymer stent is implanted into a patient, for example, following percutaneous transluminal coronary angioplasty (PTCA), 17-β-estradiol released from the stent in vivo can help to prevent post-implant restenosis in the patient. However, 17-β-estradiol is only one example of a diol with therapeutic properties that can be incorporated in the backbone of a PEU in accordance with the invention. In one aspect, any bioactive steroid-diol containing primary, secondary or phenolic hydroxyls can be used for this purpose. Many steroid esters that can be made from bioactive steroid diols for use in the invention are disclosed in European application EP 0127 829 A2.

Due to the versatility of the PEU polymers of formula (II) used in the invention compositions, the amount of the therapeutic diol incorporated in the polymer backbone can be controlled by varying the proportions of the building blocks of the polymer. For example, depending on the composition of the PEU, loading of up to 54% w/w of 17β-estradiol can be achieved.

Synthetic steroid based diols based on testosterone or cholesterol, such as 4-androstene-3, 17 diol (4-Androstenediol), 5-androstene-3, 17 diol (5-Androstenediol), 19-nor5-androstene-3, 17 diol (19-Norandrostenediol) are suitable for incorporation into the backbone of PEU polymers and surgical devices made using such polymers according to this invention. Further therapeutic diol compounds suitable for use in preparation of the invention therapeutic polymer compositions include, for example, amikacin; amphotericin B; apicycline; apramycin; arbekacin; azidamfenicol; bambermycin(s); butirosin; carbomycin; cefpiramide; chloramphenicol; chlortetracycline; clindamycin; clomocycline; demeclocycline; diathymosulfone; dibekacin, dihydrostreptomycin; dirithromycin; doxycycline; erythromycin; fortimicin(s); gentamycin(s); glucosulfone solasulfone; guamecycline; isepamicin; josamycin; kanamycin(s); leucomycin(s); lincomycin; lucensomycin; lymecycline; meclocycline; methacycline; micronomycin; midecamycin(s); minocycline; mupirocin; natamycin; neomycin; netilmicin; oleandomycin; oxytetracycline; paromycin; pipacycline; podophyllinic acid 2-ethylhydrazine; primycin; ribostamycin; rifamide; rifampin; rafamycin SV; rifapentine; rifaximin; ristocetin; rokitamycin; rolitetracycline; rasaramycin; roxithromycin; sancycline; sisomicin; spectinomycin; spiramycin; streptomycin; teicoplanin; tetracycline; thiamphenicol; theiostrepton; tobramycin; trospectomycin; tuberactinomycin; vancomycin; candicidin(s); chlorphenesin; dermostatin(s); filipin; fungichromin; missing; kanamycin(s); leucomycins(s); lincomycin; lvcensomycin; lymecycline; meclocycline; methacycline; micronomycin; midecamycin(s); minocycline; mupirocin; natamycin; neomycin; netilmicin; oleandomycin; oxytetracycline; paromomycin; pipacycline; podophyllinic acid 2-ethylhydrazine; priycin; ribostamydin; rifamide; rifampin; rifamycin SV; rifapentine; rifaximin; ristocetin; rokitamycin; rolitetracycline; rosaramycin; roxithromycin; sancycline; sisomicin; spectinomycin; spiramycin; strepton; otbramycin; trospectomycin; tuberactinomycin; vancomycin; candicidin(s); chlorphenesin; dermostatin(s); filipin; fungichromin; meparticin; mystatin; oligomycin(s); erimycin A; tubercidin; 6-azauridine; aclacinomycin(s); ancitabine; anthramycin; azacitadine; bleomycin(s) carubicin; carzinophillin A; chlorozotocin; chromomcin(s); doxifluridine; enocitabine; epirubicin; gemcitabine; mannomustine; menogaril; atorvasi pravastatin; clarithromycin; leuproline; paclitaxel; mitobronitol; mitolactol; mopidamol; nogalamycin; olivomycin(s); peplomycin; pirarubicin; prednimustine; puromycin; ranimustine; tubercidin; vinesine; zorubicin; coumetarol; dicoumarol; ethyl biscoumacetate; ethylidine dicoumarol; iloprost; taprostene; tioclomarol; amiprilose; romurtide; sirolimus (rapamycin); tacrolimus; salicyl alcohol; bromosaligenin; ditazol; fepradinol; gentisic acid; glucamethacin; olsalazine; S-adenosylmethionine; azithromycin; salmeterol; budesonide; albuteal; indinavir; fluvastatin; streptozocin; doxorubicin; daunorubicin; plicamycin; idarubicin; pentostatin; metoxantrone; cytarabine; fludarabine phosphate; floxuridine; cladriine; capecitabien; docetaxel; etoposide; topotecan; vinblastine; teniposide, and the like. The therapeutic diol can be selected to be either a saturated or an unsaturated diol.

In another embodiment, the invention provides surgical devices comprising the invention PEU polymer of structural formula (I) or (II), either alone or together with another biodegradable polymer, such as a poly(ester amide) PEA or poly(ester urethane) PEUR. The physical properties of the invention PEU polymers, such as their high molecular weight, high mechanical and compression strength, low melt viscosity and crystallinity when cured, make them particularly suitable for formation into hard tissue replacement devices. Moreover, the release of therapeutic diols and bioactive agents (e.g., for polymers having structural formula (II)), to surrounding tissues during biodegradation of an implanted surgical device aids in healing at a site of hard tissue defect into which the surgical device is implanted. The invention polymer compositions are particularly suited to formation as bone substitutes and vascular stents. The invention PEU polymer compositions can be processed from solution by pouring into a mold for the surgical device when liquid to provide the necessary mechanical strength for the surgical device. The mold and contained polymer is heated to a temperature below 200° C., as heating above about 200° C. causes PEUs to degrade due to formation of hydantoin resulting from intramolecular cyclization. Mechanical strength of the resulting polymers is illustrated by examples in Table 2.

Tensile strength of illustrative synthesized PEUs was measured and results are summarized in Table 2. Tensile strength measurement was obtained using dumbbell-shaped PEU films (4×1.6 cm), which were cast from chloroform solution with average thickness of 0.125 mm and subjected to tensile testing on tensile strength machine (Chatillon TDC200) integrated with a PC using Nexygen FM software (Amtek, Largo, Fla.) at a crosshead speed of 60 mm/min. Examples illustrated herein can be expected to have the following mechanical properties:

1. A glass transition temperature in the range from about 30° C. to about 90° C., for example, in the range from about 35° C. to about 65° C.;

2. A film of the polymer with average thickness of about 1.6 cm will have tensile stress at yield of about 20 Mpa to about 150 Mpa, for example, about 25 Mpa to about 60 Mpa;

3. A film of the polymer with average thickness of about 1.6 cm will have a percent elongation of about 10% to about 200%, for example about 50% to about 150%; and 4. A film of the polymer with average thickness of about 1.6 cm will have a Young's modulus in the range from about 500 MPa to about 2000 MPa. Table 2 below summarizes the properties of exemplary PEUs.

TABLE 2

| Polymer designation | $Tg^{a)}$ (°C.) | Tensile Stress at Yield (MPa) | Percent Elongation (%) | Young's Modulus (MPa) |
|---|---|---|---|---|
| 1-L-Leu-6 | 64 | 21 | 114 | 622 |
| [1-L-Leu-6]$_{0.75}$-[1-L-Lys(OBn)]$_{0.25}$ | 34 | 25 | 159 | 915 |

Bioactive Agents

Bioactive agents contemplated for dispersion within the polymers used in the invention therapeutic polymer compositions include anti-proliferants, rapamycin and any of its analogs or derivatives, paclitaxel or any of its taxene analogs or derivatives, everolimus, sirolimus, tacrolimus, or any of its -limus named family of drugs, and statins such as simvastatin, atorvastatin, fluvastatin, pravastatin, lovastatin, rosuvastatin, geldanamycins, such as 17AAG (17-allylamino-17-demethoxygeldanarnycin); Epothilone D and other epothilones, 17-dimethylaminoethylamino-17-demethoxygeldanamycin and other polyketide inhibitors of heat shock protein 90 (Hsp90), cilostazol, and the like.

Suitable bioactive agents for dispersion in the invention therapeutic polymer compositions and particles made therefrom also can be selected from those that promote endogenous production of a therapeutic natural wound healing agents, such as nitric oxide, which is endogenously produced by endothelial cells. Alternatively the bioactive agents released from the polymers during degradation may be directly active in promoting natural wound healing processes by endothelial cells. These bioactive agents can be any agent that donates, transfers, or releases nitric oxide, elevates endogenous levels of nitric oxide, stimulates endogenous synthesis of nitric oxide, or serves as a substrate for nitric oxide synthase or that inhibits proliferation of smooth muscle cells. Such agents include, for example, aminoxyls, furoxans, nitrosothiols, nitrates and anthocyanins; nucleosides such as adenosine and nucleotides such as adenosine diphosphate (ADP) and adenosine triphosphate (ATP); neurotransmitter/neuromodulators such as acetylcholine and 5-hydroxytryptamine (serotonin/5-HT); histamine and catecholamines such as adrenalin and noradrenalin; lipid molecules such as sphingosine-1-phosphate and lysophosphatidic acid; amino acids such as arginine and lysine; peptides such as the bradykinins, substance P and calcium gene-related peptide (CGRP), and proteins such as insulin, vascular endothelial growth factor (VEGF), and thrombin.

A variety of bioactive agents and ligands for bioactive agents can be attached covalently, for example, to the surface of particles or devices containing polymers of structural formula (II). Bioactive agents, such as targeting antibodies, polypeptides (e.g., antigens) and drugs can be covalently conjugated to the surface of the polymers. In addition, coating molecules, such as polyethylene glycol (PEG) as a ligand for attachment of antibodies or polypeptides or phosphatidylcholine (PC) as a means of blocking attachment sites on the surface of the polymers, can be surface-conjugated thereto.

For example, small proteinaceous motifs, such as the B domain of bacterial Protein A and the functionally equivalent region of Protein G are known to bind to, and thereby capture, antibody molecules by the Fc region. Such proteinaceous motifs can be attached as bioactive agents to the invention polymers of structural formula (II), especially to the surface of such polymers, as described herein. Such molecules will act, for example, as ligands to attach antibodies for use as targeting ligands or to capture antibodies to hold precursor cells or capture cells out of the blood stream. Therefore, the antibody types that can be attached to polymers using a Protein A or Protein G functional region are those that contain an Fc region. The capture antibodies will in turn bind to and hold precursor cells, such as progenitor cells, near the polymer surface while the precursor cells secrete various factors and interact with other cells of the subject into which devices made using the invention polymers of structural formula (II) are implanted. In addition, one or more bioactive agents, such as the bradykinins, may activate the precursor cells.

In addition, bioactive agents for attaching precursor cells or for capturing progenitor endothelial cells (PECs) from a blood stream in a subject implanted with a surgical device made using the invention polymers of structural formula (II) are monoclonal antibodies directed against a known precursor cell surface marker. For example, complementary determinants (CDs) that have been reported to decorate the surface of endothelial cells include CD31, CD34, CD102, CD105, CD106, CD109, CD130, CD141, CD142, CD143, CD144, CDw145, CD146, CD147, and CD166. These cell surface markers can be of varying specificity and the degree of specificity for a particular cell/developmental type/stage is in many cases not fully characterized. In addition, these cell marker molecules against which antibodies have been raised will overlap (in terms of antibody recognition) especially with CDs on cells of the same lineage: monocytes in the case of endothelial cells. Circulating endothelial progenitor cells are some way along the developmental pathway from (bone marrow) monocytes to mature endothelial cells. CDs 106, 142 and 144 have been reported to mark mature endothelial cells with some specificity. CD34 is presently known to be specific for progenitor endothelial cells and therefore is currently preferred for capturing progenitor endothelial cells out of blood in the site into which devices, such as hard tissue replacement implants made using the invention polymers particles are implanted for local delivery of the active agents. Examples of such antibodies include single-chain antibodies, chimeric antibodies, monoclonal antibodies, polyclonal antibodies, antibody fragments, Fab fragments, IgA, IgG, IgM, IgD, IgE and humanized antibodies, and active fragments thereof.

The following bioactive agents and small molecule drugs will also be particularly effective for conjugation to the invention PEU polymers of structural formula (II), for use in implantable surgical devices. Such bioactive agent(s) will be selected for suitable therapeutic or palliative effect in treatment of a disease of interest, or symptoms thereof, or in experiments designed for in vitro testing of such effects in cells or tissue culture, or in vivo.

In one embodiment, the suitable bioactive agents are not limited to, but include, various classes of compounds that facilitate, or contribute to, wound healing when presented in a time-release fashion. Such bioactive agents include ligands for wound-healing cells, including certain precursor cells. Such wound healing cells include, for example, pericytes and endothelial cells, as well as inflammatory healing cells. To recruit such cells to the site of a surgical device, such as a bone substitute in vivo, the polymer compositions used in the invention surgical devices and methods of use can include ligands for such cells, such as antibodies and smaller molecule ligands, that specifically bind to "cellular adhesion molecules" (CAMs). Exemplary ligands for wound healing cells include those that specifically bind to Intercellular adhesion molecules (ICAMs), such as ICAM-1 (CD54 antigen); ICAM-2 (CD102 antigen); ICAM-3 (CD50 antigen); ICAM-4 (CD242 antigen); and ICAM-5; Vascular cell adhesion molecules (VCAMs), such as VCAM-1 (CD106 antigen); Neural cell adhesion molecules (NCAMs), such as NCAM-1 (CD56 antigen); or NCAM-2; Platelet endothelial cell adhesion molecules PECAMs, such as PECAM-1 (CD31 antigen); Leukocyte-endothelial cell adhesion molecules (ELAMs), such as LECAM-1; or LECAM-2 (CD62E antigen), and the like.

In another aspect, the suitable bioactive agents include extra cellular matrix proteins, macromolecules that can be attached covalently to the polymers used in the invention surgical devices. Examples of useful extra-cellular matrix proteins include, for example, glycosaminoglycans, usually linked to proteins (proteoglycans), and fibrous proteins (e.g., collagen; elastin; fibronectins and laminin). Bio-mimics of extra-cellular proteins can also be used. These are usually non-human, but biocompatible, glycoproteins, such as alginates and chitin derivatives. Wound healing peptides that are specific fragments of such extra-cellular matrix proteins and/or their bio-mimics can also be used.

Proteinaceous growth factors are another category of bioactive agents suitable for attachment to the invention PEU polymer compositions and surgical devices made using such polymer compositions. Such bioactive agents are effective in promoting wound healing and other disease states as is known in the art, for example, Platelet Derived Growth Factor-BB (PDGF-BB), Tumor Necrosis Factor-alpha (TNF-alpha), Epidermal Growth Factor (EGF), Keratinocyte Growth Factor (KGF), Thymosin B4; and, various angiogenic factors such as vascular Endothelial Growth Factors (VEGFs), Fibroblast Growth Factors (FGFs), Tumor Necrosis Factor-beta (TNF-beta), and Insulin-like Growth Factor-1 (IGF-1). Many of these proteinaceous growth factors are available commercially or can be produced recombinantly using techniques well known in the art.

Growth factors, such as VEGFs, PDGFs, FGF, NGF, and evolutionary and functionally related biologics, and angiogenic enzymes, such as thrombin, may also be used as bioactive agents in the invention.

Small molecule drugs are yet another category of bioactive agents suitable for covalent attachment to polymers of the invention as described herein. Such drugs include, for example, antimicrobials and anti-inflammatory agents as well as certain healing promoters, such as, for example, vitamin A and synthetic inhibitors of lipid peroxidation.

A variety of antibiotics can be conjugated covalently as bioactive agents in the invention polymer compositions to indirectly promote natural healing processes by preventing or controlling infection at a site of implant of a surgical device made using the polymer composition. Suitable antibiotics include many classes, such as aminoglycoside antibiotics or quinolones or beta-lactams, such as cefalosporins, e.g., ciprofloxacin, gentamycin, tobramycin, erythromycin, vancomycin, oxacillin, cloxacillin, methicillin, lincomycin, ampicillin, and colistin. Suitable antibiotics have been described in the literature and include, for example, Adriamycin PFS/RDF® (Pharmacia and Upjohn), Blenoxane® (Bristol-Myers Squibb Oncology/Immunology), Cerubidine® (Bedford), Cosmegen® (Merck), DaunoXome® (NeXstar), Doxil® (Sequus), Doxorubicin Hydrochloride® (Astra), Idamycin® PFS (Pharmacia and Upjohn), Mithracin® (Bayer), Mitamycin® (Bristol-Myers Squibb Oncology/Immunology), Nipen® (SuperGen), Novantrone® (Immunex) and Rubex® (Bristol-Myers Squibb Oncology/Immunology). In one embodiment, the peptide can be a glycopeptide. "Glycopeptide" refers to oligopeptide (e.g. heptapeptide) antibiotics, characterized by a multi-ring peptide core optionally substituted with saccharide groups, such as vancomycin.

Examples of glycopeptides included in this category of antimicrobials may be found in "Glycopeptides Classification, Occurrence, and Discovery," by Raymond C. Rao and Louise W. Crandall, ("Bioactive agents and the Pharmaceutical Sciences" Volume 63, edited by Ramakrishnan Nagarajan, published by Marcal Dekker, Inc.). Additional examples of glycopeptides are disclosed in U.S. Pat. Nos. 4,639,433; 4,643,987; 4,497,802; 4,698,327, 5,591,714; 5,840,684; and 5,843,889; in EP 0 802 199; EP 0 801 075; EP 0 667 353; WO 97/28812; WO 97/38702; WO 98/52589; WO 98/52592; and in *J. Amer. Chem. Soc.* (1996) 118: 13107-13108; *J Amer. Chem. Soc.* (1997) 119:12041-12047; and *J. Amer. Chem. Soc.* (1994) 116:4573-4590. Representative glycopeptides include those identified as A477, A35512, A40926, A41030, A42867, A47934, A80407, A82846, A83850, A84575, AB-65, Actaplanin, Actinoidin, Ardacin, Avoparcin, Azureomycin, Balhimyein, Chloroorientiein, Chloropolysporin, Decaplanin, demethylvancomycin, Eremomycin, Galacardin, Helvecardin, Izupeptin, Kibdelin, LL-AM374, Mannopeptin, MM45289, MM47756, MM47761, MM49721, MM47766, MM55260, MM55266, MM55270, MM56597, MM56598, OA-7653, Orenticin, Parvodicin, Ristocetin, Ristomycin, Synmonicin, Teicoplanin, UK-68597, UD-69542, UK-72051, Vancomycin, and the like. The term "glycopeptide" or "glycopeptide antibiotic" as used herein is also intended to include the general class of glycopeptides disclosed above on which the sugar moiety is absent, i.e. the aglycone series of glycopeptides. For example, removal of the disaccharide moiety appended to the phenol on vancomycin by mild hydrolysis gives vancomycin aglycone. Also included within the scope of the term "glycopeptide antibiotics" are synthetic derivatives of the general class of glycopeptides disclosed above, including alkylated and acylated derivatives. Additionally, within the scope of this term are glycopeptides that have been further appended with additional saccharide residues, especially aminoglycosides, in a manner similar to vancosamine.

The term "lipidated glycopeptide" refers specifically to those glycopeptide antibiotics that have been synthetically modified to contain a lipid substituent. As used herein, the term "lipid substituent" refers to any substituent contains 5 or more carbon atoms, preferably, 10 to 40 carbon atoms. The lipid substituent may optionally contain from 1 to 6 heteroatoms selected from halo, oxygen, nitrogen, sulfur, and phosphorous. Lipidated glycopeptide antibiotics are well known in the art. See, for example, in U.S. Pat. Nos. 5,840,684, 5,843,889, 5,916,873, 5,919,756, 5,952,310, 5,977,062, 5,977,063, EP 667,353, WO 98/52589, WO 99/56760, WO 00/04044, WO 00/39156.

Anti-inflammatory bioactive agents are also useful for use in invention polymer compositions and surgical devices. Depending on the body site of implant, such anti-inflammatory bioactive agents include, e.g. analgesics (e.g., NSAIDS and salicyclates), steroids, antirheumatic agents, gastrointestinal agents, gout preparations, hormones (glucocorticoids), nasal preparations, ophthalmic preparations, otic preparations (e.g., antibiotic and steroid combinations), respiratory agents, and skin & mucous membrane agents. See, *Physician's Desk Reference*, 2005 Edition. Specifically, the anti-inflammatory agent can include dexamethasone, which is chemically designated as (11Θ, 16I)-9-fluro-11,17,21-trihydroxy-16-methylpregna-1,4-diene-3,20-dione. Alternatively, the anti-inflammatory bioactive agent can be or include sirolimus (rapamycin), which is a triene macrolide antibiotic isolated from *Streptomyces hygroscopicus*.

The polypeptide bioactive agents included in the invention compositions, surgical devices and methods can also include "peptide mimetics." Such peptide analogs, referred to herein as "peptide mimetics" or "peptidomimetics," are commonly used in the pharmaceutical industry with properties analogous to those of the template peptide (Fauchere, J. (1986) Adv. *Bioactive agent Res.*, 15:29; Veber and Freidinger (1985) *TINS*, p. 392; and Evans et al. (1987) *J. Med. Chem.*, 30:1229) and are usually developed with the aid of computerized molecular modeling. Generally, peptidomimetics are structurally similar to a paradigm polypeptide (i.e., a polypeptide that has a biochemical property or pharmacological activity), but have one or more peptide linkages optionally replaced by a linkage selected from the group consisting of: —CH$_2$NH—, —CH$_2$S—, CH$_2$—H$_2$—, —CH=CH— (cis and trans), —COCH$_2$—, —CH(OH)CH$_2$—, and —CH$_2$SO—, by methods known in the art and further described in the following references: Spatola, A. F. in *Chemistry and Biochemistry of Amino Acids, Peptides, and Proteins*, B. Weinstein, eds., Marcel Dekker, New York, p. 267 (1983); Spatola, A. F., *Vega Data* (March 1983), Vol. 1, Issue 3, "Peptide Backbone Modifications" (general review); Morley, J. S., *Trends. Pharm. Sci.*, (1980) pp. 463-468 (general review); Hudson, D. et al., *Int. J. Pept. Prot. Res.*, (1979) 14:177-185 (—CH$_2$NH—, CH$_2$CH$_2$—); Spatola, A. F. et al., *Life Sci.*, (1986) 38:1243-1249 (—CH$_2$—S—); Harm, M. M., *J. Chem. Soc. Perkin Trans I* (1982) 307-314 (—CH=CH—, cis and trans); Almquist, R. G. et al., *J. Med. Chem.*, (1980) 23:2533 (—COCH$_2$—); Jennings-Whie, C. et al., *Tetrahedron Lett.*, (1982) 23:2533 (—COCH$_2$—); Szelke, M. et al., European Appln., EP 45665 (1982) CA: 97:39405 (1982) (—CH(OH)CH$_2$—); Holladay, M. W. et al., *Tetrahedron Lett.*, (1983) 24:4401-4404 (—C(OH)CH$_2$—); and Hruby, V. J., *Life Sci.*, (1982) 31:189-199 (—CH$_2$—S—). Such peptide mimetics may have significant advantages over natural polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others.

Additionally, substitution of one or more amino acids within a peptide (e.g., with a D-lysine in place of L-lysine) may be used to generate more stable peptides and peptides resistant to endogenous peptidases. Alternatively, the synthetic polypeptides covalently bound to the biodegradable polymer, can also be prepared from D-amino acids, referred to as inverso peptides. When a peptide is assembled in the opposite direction of the native peptide sequence, it is referred to as a retro peptide. In general, polypeptides prepared from D-amino acids are very stable to enzymatic hydrolysis. Many cases have been reported of preserved biological activities for retro-inverso or partial retro-inverso polypeptides (U.S. Pat. No. 6,261,569 B1 and references therein; B. Fromme et al, *Endocrinology* (2003)144:3262-3269.

The following examples are meant to illustrate, and not to limit, the invention.

Example 1

Monomer Synthesis

Preparation of Di-p-Toluenesulfonic Acid Salt of Bis-L-Leucine-Hexane-1,6-Diester Synthesis of tosylate salts of diamines as nucleophilic monomers has been described previously, for example in U.S. Pat. No. 6,503,538 B1. Di-p-toluenesulfonic acid salt of bis-L-leucine-hexane-1,6-diester (compound 1) was prepared by a modification of the previously published method.

Compound 1

L-leucine (0.132 mol), p-toluenesulfonic acid monohydrate (0.132 mol) and 1,6-hexane diol (0.06 mol) in 250 mL of toluene were placed in a flask equipped with a Dean-Stark apparatus and overhead stirrer. The heterogeneous reaction mixture was heated to reflux for about. 12 h until 4.3 mL (0.24 mol) of water evolved. The reaction mixture was then cooled to room temperature, filtered, washed with acetone and recrystallized twice from methanol/toluene 2:1 mix. Yields and Mp were identical to published data (R. Katsarava et al. *J. Polym. Sci., Part A: Polym. Chem.* (1999) 37:391-407).

Preparation of Di-p-Toluenesulfonic Acid Salt of L-Lysine Benzyl Ester (L-Lys(OBn)

Di-p-toluenesulfonic acid salt of L-lysine benzyl ester (Compound 2) was prepared as described previously in U.S. Pat. No. 6,503,538 B1 by refluxing of benzyl alcohol, toluenesulfonic acid monohydrate and L-lysine monohydrochloride in toluene, while applying azeotropic removal of water.

Compound 2

Example 2

Preparation of PEU 1-L-Leu-6 (Polymer Entry #2, Table 1)

Figure 1:
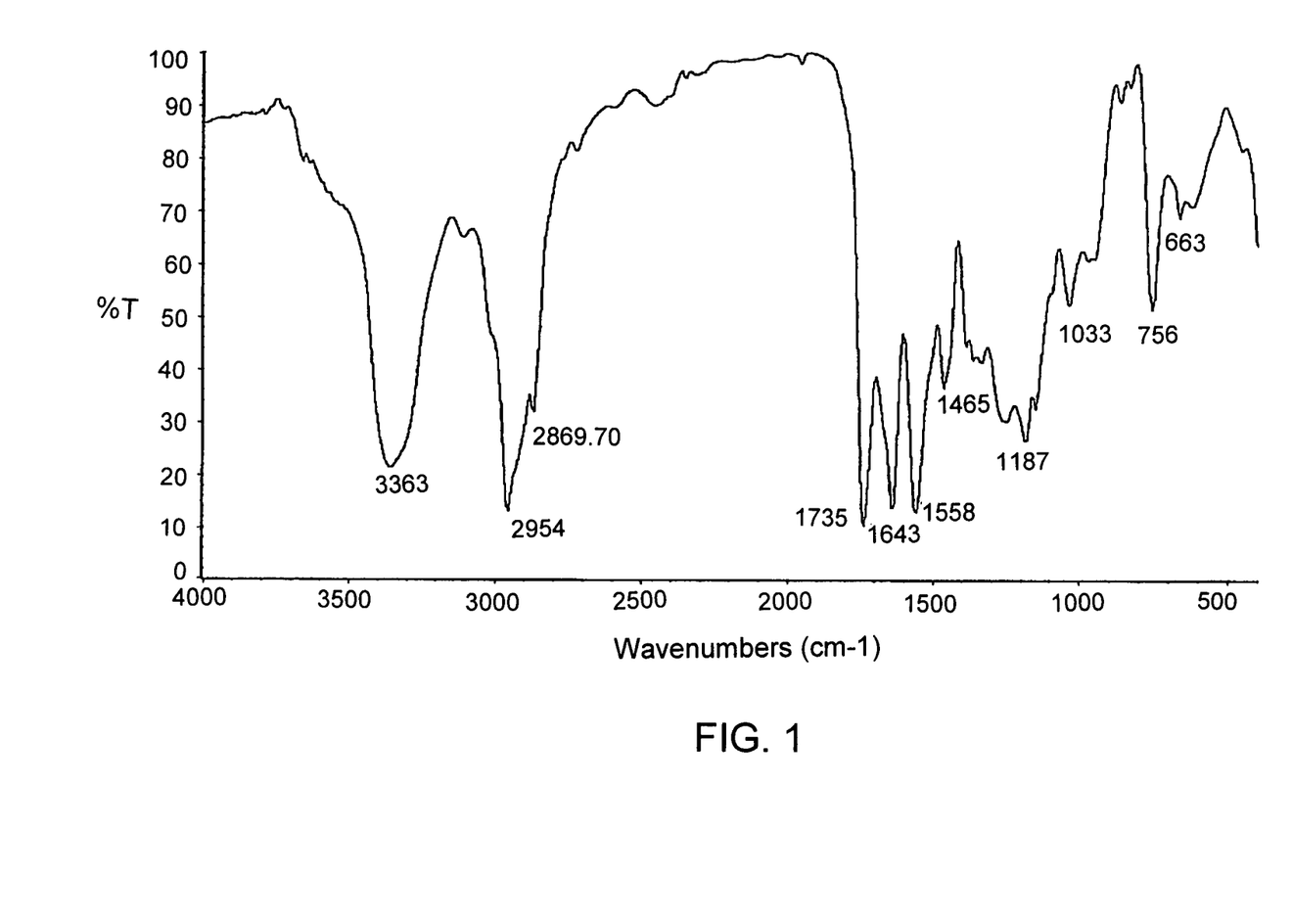
FIG. 1 is a graph showing a FT-IR spectrum (film on NaCl plate) of poly(ester urea) (PEU) 1-L-Leu-4. (Table 1, entry #1)
Figure 2:
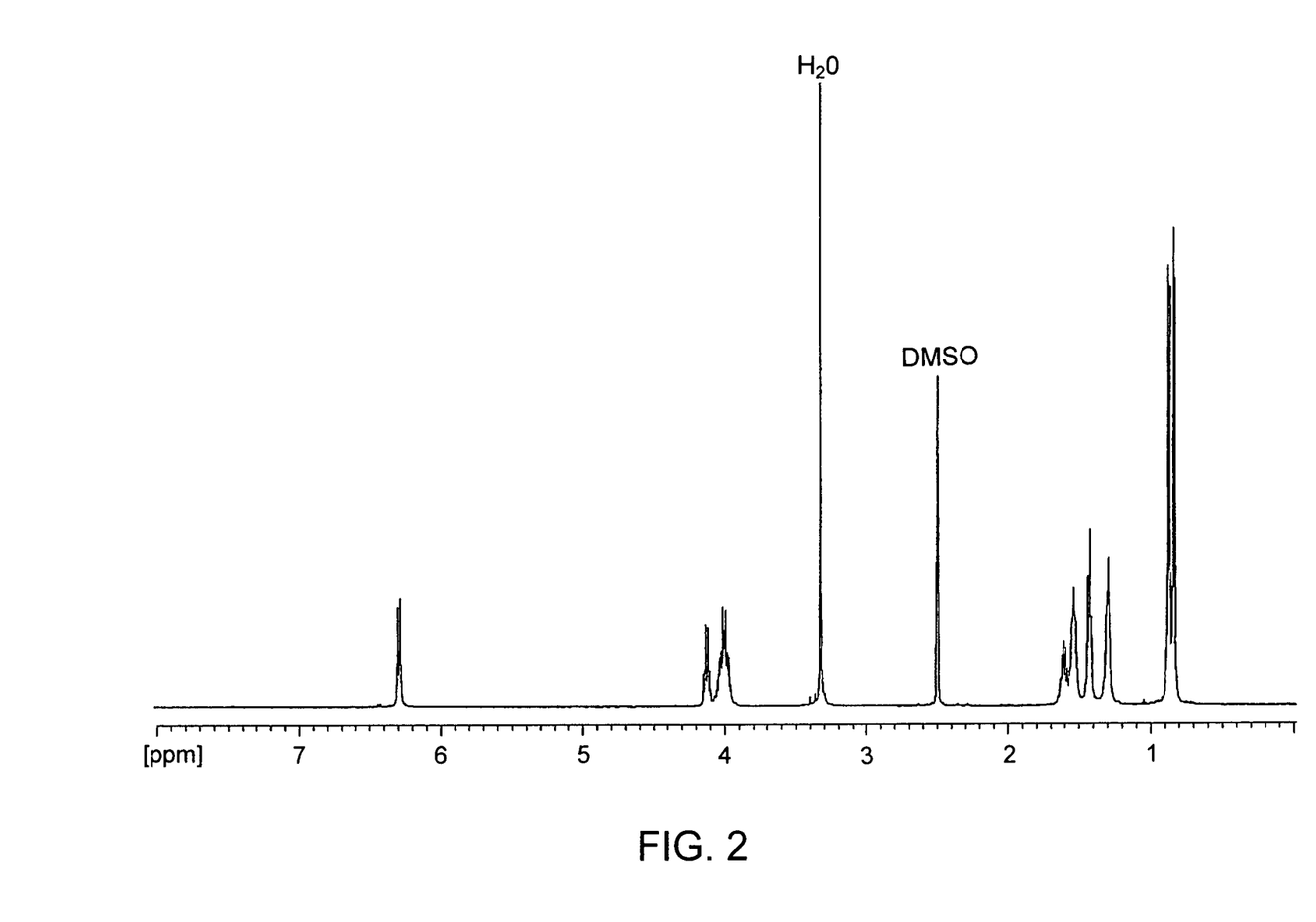
FIG. 2 is a graph showing a $^1$H NMR (500 MHz, DMSO-$d_6$) spectrum of poly(ester urea) 1-Leu-6. (Table 1, entry #2)
Figure 3:
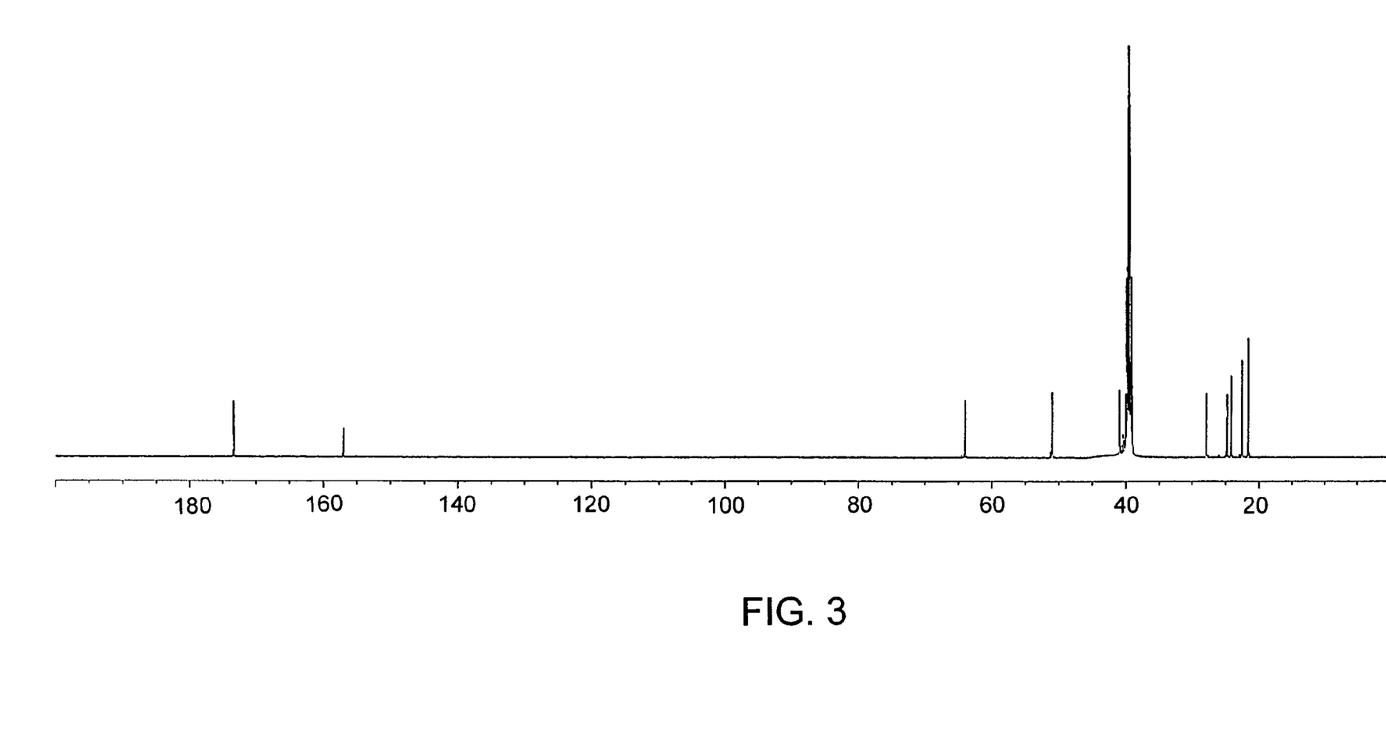
FIG. 3 is a graph showing a $^{13}$C NMR (125 MHz MHz, DMSO-$d_6$) spectrum of poly(ester urea) 1-Leu-6. (Table 1, entry #2)
Figure 4:
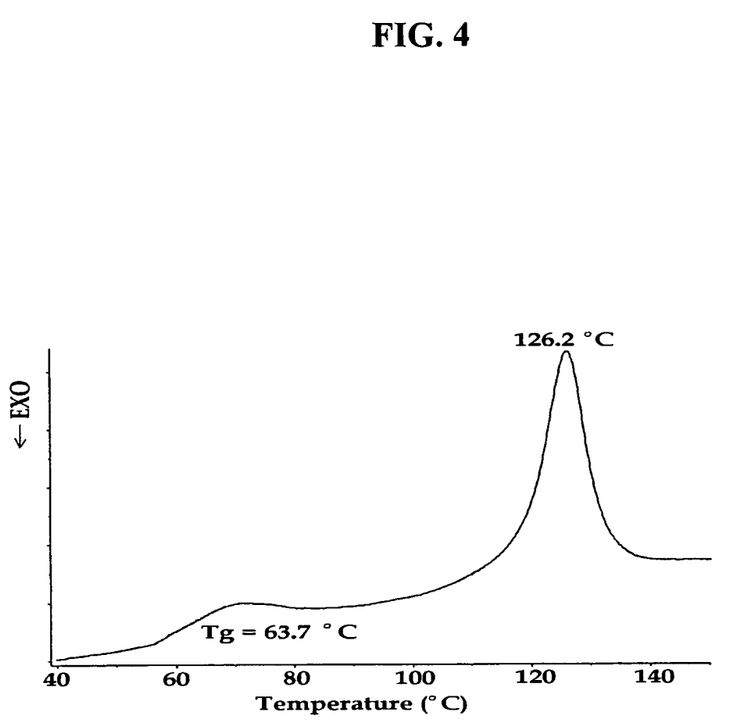
FIG. 4 is a graph showing a Differential Scanning Calorimetry trace of poly(ester urea) 1-Leu-6, first heating, heating rate 10° C./min. (Table 1, entry #2)

To a suspension of 6.89 g (10 mmol) of di-p-toluenesulfonic acid salt of bis(L-leucine)-1,6-hexanediol-diester in 150 mL of water, 4.24 g (40 mmol) of anhydrous sodium carbonate was added, stirred at room temperature for 30 min. and cooled to 2° C. to 0° C. In parallel, a solution of 0,9893 g (10 mmol) of phosgene in 35 mL of chloroform was cooled to 15° C. to 10° C. The first solution was placed into a reactor for interfacial polycondensation and the second solution was quickly added in bolus and stirred briskly for 15 min. Then the chloroform layer was separated, dried, over anhydrous $Na_2SO_4$, and filtered. The obtained solution was evaporated and the polymer yield was dried in vacuum at 45° C. Yield was 82%. For $^1H$ and $^{13}C$ NMR see FIG. 2 and FIG. 3. Elemental analysis: for $C_{19}H_{34}N_2O_5$, calculated values: C: 61.60%, H: 9.25%, N: 7.56%. Found values: C: 61.63%, H: 8.90%, N: 7.60.

Example 3

Preparation of PEU 1-L-Leu-DAS (Polymer: Entry #5, Table 1)

Compound 4

A cooled solution (ice-bath) of 5 g (6.975 mmole) of bis (L-leucine)-1,4:3,6-dianhydrosorbitol-diester and 2.4 g of sodium carbonate in 40 mL of water was prepared. To the cooled solution, 70 mL of chloroform was added with vigorous stirring and then 3.7 mL of 20% phosgene solution in toluene (Fluka) was introduced. Poly(ester urea) formed rapidly with evolution of heat. After the reaction had been stirred for 10 min, the organic layer was rotoevaporated and residual polymer was filtered, washed several times with water, and dried in vacuum over night. Yield of product was 1.6 g. (57%). Polymer properties are as summarized in Table 1.

Example 4

Figure 5:
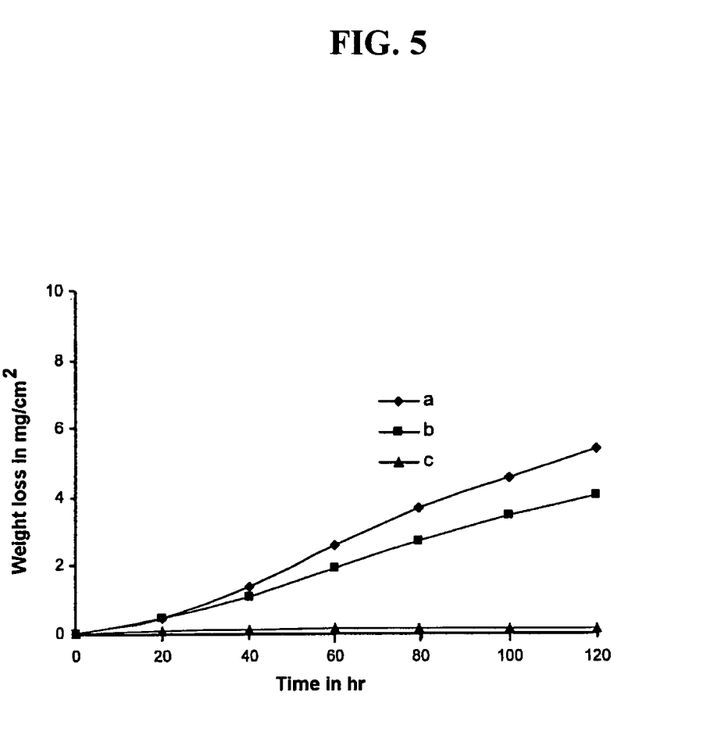
FIG. 5 is a graph showing in vitro biodegradation of a polymer film of PEU 1-L-Leu-4 (Table 1, entry #1) subjected to: a) α-chymotrypsin solution in buffer, b) lipase solution in buffer, c) pure buffer (0.2 M phosphate buffer with ph 7.4)

This example describes a degradation study conducted to compare degradation rates over time of a PEU polymer 1-L-Leu-4 (Table 1, entry #1). Circular PEU films of 4 cm diameter and 400-500 mg each, were placed into glass beakers containing 10 ml of 0.2 M phosphate buffer solution of pH 7.4 either with 4 mg of an enzyme (α-chymotrypsin or lipase) or control enzyme-free buffer. The glass vessels were maintained at 37° C. Films were removed from the enzyme solutions after predetermined times (at 20, 40, 60, 80, 100 and 120 minutes), dried up to constant weights, and weighed. Then the films were placed into the fresh solution of either enzyme or pure buffer and all the procedures described above were repeated. Repeat count corresponds to the number of experimental points in FIG. 5 and FIG. 6. Weight changes per unit surface area of the sample indicate loss of sample by biodegradation were calculated and represented graphically vs. biodegradation time (FIG. 5 and FIG. 6). The results of the study show that the PEU polymer has a degradation profile that is almost zero order, corresponding to a surface degradation profile.

All publications, patents, and patent documents are incorporated by reference herein, as though individually incorporated by reference. The invention has been described with reference to various specific and preferred embodiments and techniques. However, it should be understood that many variations and modifications might be made while remaining within the spirit and scope of the invention.

Although the invention has been described with reference to the above examples, it will be understood that modifications and variations are encompassed within the spirit and scope of the invention. Accordingly, the invention is limited only by the following claims.

What is claimed is:

1. A crystalline or semi-crystalline poly(ester urea) (PEU) polymer composition having formula (II):

Formula (II)

wherein m is about 0.1 to about 0.9; p is about 0.9 to about 0.1; n is about 10 to about 150;

$R^1$ is independently ($C_2$-$C_{20}$) alkylene, ($C_2$-$C_{20}$) alkenylene, ($C_2$-$C_8$) alkyloxy, ($C_2$-$C_{20}$) alkylene, a residue of a saturated or unsaturated therapeutic diol, or a bicyclic-fragment of 1,4:3,6-dianhydrohexitol of formula (III):

Formula (III)

each $R^2$ is independently hydrogen, ($C_1$-$C_{12}$) alkyl or ($C_6$-$C_{10}$) aryl;

the $R^3$s, in an individual m monomer, are independently hydrogen, ($C_1$-$C_6$) alkyl, ($C_2$-$C_6$) alkenyl, ($C_2$-$C_6$) alkynyl, or ($C_6$-$C_{10}$) aryl ($C_1$-$C_6$) alkyl; and $R^4$ is independently ($C_2$-$C_{20}$) alkyl or ($C_2$-$C_{20}$) alkenyl, wherein the composition has a molecular weight in the range from about 75,000 Da to about 200,000 Da, as measured by gel permeation chromatography and wherein the composition has a tensile strength at break in the range from about 20 MPa to about 150 MPa as measured by tensile measurement.

2. The composition of claim 1, wherein $R^4$ is independently ($C_2$-$C_{20}$) alkyl.

3. The composition of claim 1, wherein $R^4$ is independently ($C_3$ to $C_6$) alkyl or ($C_3$ to $C_6$) alkenyl.

4. The composition of claim 1, wherein $R^4$ is independently —$(CH_2)_4$—.

5. The composition of claim 1, wherein $R^3$ is $CH_2Ph$.

6. The composition of claim 1, wherein the bicyclic fragment of 1,4:3,6-dianhydrohexitol of formula (III) is derived from D-glucitol, D-mannitol, or L-iditol.

7. The composition of claim 1, wherein the $R^1$ is a residue of a saturated or unsaturated therapeutic diol or a bicyclic-fragment of 1,4:3,6-dianhydrohexitol of formula (III).

8. The composition of claim 7, wherein the bicyclic-fragment of 1,4:3,6-dianhydrohexitol is a residue of 1,4:3,6-dianhydrosorbitol.

9. The composition of claim 1, wherein the composition biodegrades over a period of about two weeks to about 9 months.

10. The composition of claim 1, wherein the composition further comprises at least one bioactive agent covalently attached to the polymer of formula (II).

11. A surgical device comprising a polymer of claim 1, wherein the device is implantable.

12. The device of claim 11, wherein the surgical device is completely biodegradable.

13. The device of claim 11, wherein the surgical device is a bone substitute.

14. The device of claim 11, wherein the implantable surgical device is a vascular stent.

15. The device of claim 11, wherein the device is a hard tissue replacement implant.

16. The device of claim 11, wherein the device is a bone substitute.

17. The device of claim 11, wherein the device biodegrades over a period of about two weeks to about six years.

18. The device of claim 11, wherein at least one of $R^1$ is a therapeutic diol, wherein the device biodegrades to release the therapeutic diol.

19. The device of claim 18, wherein the therapeutic diol is 17-beta-Estradiol.

20. The device of claim 11, wherein the polymer has a chemical formula described by structural formula (II) and wherein the composition further comprises at least one bioactive agent conjugated to the polymer.

21. The device of claim 20, wherein the bioactive agent is an antibiotic.

22. The device of claim 20, wherein the bioactive agent is an analgesic.

\* \* \* \* \*